United States Patent [19]

Bundy

[11] 4,192,948

[45] Mar. 11, 1980

[54] TRANS-2,3-DIDEHYDRO-9-DEOXY-9-METHYLENE-ω-ARYL-PGF COMPOUNDS

[75] Inventor: Gordon L. Bundy, Portage, Mich.

[73] Assignee: The Upjohn Company, Kalamazoo, Mich.

[21] Appl. No.: 932,999

[22] Filed: Aug. 11, 1978

Related U.S. Application Data

[62] Division of Ser. No. 893,771, Apr. 5, 1978, Pat. No. 5,165,436.

[51] Int. Cl.$^2$ ............................................. C07C 177/00
[52] U.S. Cl. .................................... 560/55; 260/408; 260/410; 260/410.5; 260/410.9 R; 260/413; 562/465
[58] Field of Search ................. 560/55; 260/408, 410, 260/410.5, 410.9, 413; 562/465

*Primary Examiner*—Paul J. Killos
*Attorney, Agent, or Firm*—Robert A. Armitage

[57] ABSTRACT

The present specification relates to novel 9-deoxy-9-methylene-trans-2,3-didehydro-PGF compounds with improved pharmacological properties. While these compounds are useful in inducing a wide variety of prostaglandin-like pharmacological effects, they are specifically useful as regulators of procreation and fertility.

17 Claims, No Drawings

TRANS-2,3-DIDEHYDRO-9-DEOXY-9-METHYLENE-ω-ARYL-PGF COMPOUNDS

The present application is a divisional application of Ser. No. 893,771, filed Apr. 5, 1978, now U.S. Pat. No. 5,165,436, issued Aug. 21, 1979.

The present invention relates to prostaglandin analogs, for which the essential material constituting disclosure therefor is incorporated by reference here from U.S. Pat. No. 4,165,436.

I claim:

1. A prostaglandin analog of the formula

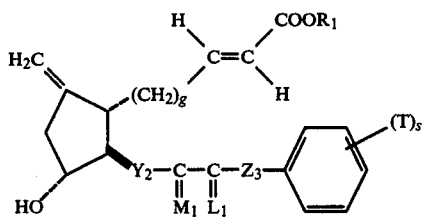

wherein $Y_2$ is trans—CH=CH—, —CH$_2$CH$_2$—, or cis—CH=CH—;
wherein $M_1$ is

or

wherein $R_5$ is hydrogen or methyl;
wherein $L_1$ is

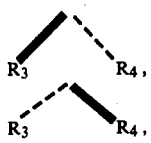

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein g is 4, 5, or 6,
wherein $Z_3$ is oxa or —(CH$_2$)$_h$—,
wherein h is zero, one, two, or three; wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $Z_3$ is oxa only when $R_3$ and $R_4$ are hydrogen or methyl, being the same or different; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation.

2. A prostaglandin analog according to claim 1, wherein $Z_3$ is —(CH$_2$)$_h$.

3. trans-2,3-Didehydro-9-deoxy-9-methylene-17-phenyl-18,19,20-trinor-PGF$_1$, a prostaglandin analog according to claim 2.

4. A prostaglandin analog according to claim 1, wherein $Z_3$ is oxa.

5. A prostaglandin analog according to claim 1, wherein g is 4.

6. A prostaglandin analog according to claim 5, wherein $Y_2$ is —CH$_2$CH$_2$—.

7. trans-2,3-Didehydro-9-deoxy-9-methylene-13,14-dihydro-16-phenoxy-17,18,19,20-tetranor-PGF$_1$, a prostaglandin analog according to claim 6.

8. A prostaglandin analog according to claim 5, wherein $Y_1$ is trans—CH=CH—.

9. A prostaglandin analog according to claim 8, wherein at least one of $R_3$ and $R_4$ is methyl.

10. trans-2,3-Didehydro-9-deoxy-9-methylene-16,16-dimethyl-16-phenoxy-17,18,19,20-tetranor-PGF$_1$, a prostaglandin analog according to claim 9.

11. trans-2,3-Didehydro-9-deoxy-9-methylene-16,16-dimethyl-16-phenoxy-17,18,19,20-tetranor-PGF$_1$, methyl ester, a prostaglandin analog according to claim 9.

12. A prostaglandin analog according to claim 8, wherein $R_3$ and $R_4$ are both hydrogen.

13. A prostaglandin analog according to claim 12, wherein $R_5$ is methyl.

14. trans-2,3-Didehydro-9-deoxy-9-methylene-15-methyl-16-phenoxy-17,18,19,20-tetranor-PGF$_1$, a prostaglandin analog according to claim 13.

15. A prostaglandin analog according to claim 14, wherein $R_5$ is hydrogen.

16. trans-2,3-Didehydro-9-deoxy-9-methylene-16-phenoxy-17,18,19,20-tetranor-PGF$_1$, methyl ester, a prostaglandin analog according to claim 15.

17. trans-2,3-Didehydro-9-deoxy-9-methylene-16-phenoxy-17,18,19,20-tetranor-PGF$_1$, a prostaglandin analog according to claim 15.

* * * * *

UNITED STATES PATENT OFFICE
CERTIFICATE OF CORRECTION

Patent No. 4,192,948     Dated  11 March 1980

Inventor(s)  Gordon L. Bundy

It is certified that error appears in the above-identified patent and that said Letters Patent are hereby corrected as shown below:

In the Related U.S. Application Data and at column 1, line 7, "Pat. No. 5,165,436" should read -- Pat. No. 4,165,436 --.

Signed and Sealed this

Ninth Day of September 1980

[SEAL]

Attest:

Attesting Officer

SIDNEY A. DIAMOND

Commissioner of Patents and Trademarks